(12) United States Patent
Makino

(10) Patent No.: US 10,402,947 B2
(45) Date of Patent: Sep. 3, 2019

(54) IMAGE PROCESSING APPARATUS AND ELECTRONIC ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 78 days.

(21) Appl. No.: 15/556,420

(22) PCT Filed: Jul. 18, 2017

(86) PCT No.: PCT/IB2017/054320
§ 371 (c)(1),
(2) Date: Sep. 7, 2017

(87) PCT Pub. No.: WO2017/208215
PCT Pub. Date: Dec. 7, 2017

(65) Prior Publication Data
US 2018/0189933 A1      Jul. 5, 2018

(30) Foreign Application Priority Data

Jun. 2, 2016    (JP) .................................. 2016-110887

(51) Int. Cl.
*G06T 5/00*       (2006.01)
*A61B 1/045*      (2006.01)
(Continued)

(52) U.S. Cl.
CPC .......... *G06T 5/002* (2013.01); *A61B 1/00006* (2013.01); *A61B 1/00009* (2013.01);
(Continued)

(58) Field of Classification Search
CPC ......... G06T 5/002; G06T 5/001; G06T 5/003; G06T 5/004
(Continued)

(56) References Cited

U.S. PATENT DOCUMENTS

| 2005/0117036 A1* | 6/2005 | Nishi | H04N 9/045 348/241 |
| 2005/0117812 A1* | 6/2005 | Nishi | H04N 19/176 382/268 |

(Continued)

FOREIGN PATENT DOCUMENTS

| JP | 2008-124976 | 5/2008 |
| JP | 2013-089205 | 5/2013 |

(Continued)

OTHER PUBLICATIONS

U.S. Appl. No. 15/556,425 to Takao Makino, filed Sep. 7, 2017.

(Continued)

*Primary Examiner* — Dwayne D Bost
*Assistant Examiner* — Stephen M Brinich
(74) *Attorney, Agent, or Firm* — Greenblum & Bernstein, P.L.C.

(57) ABSTRACT

Provided are an image processing device and an electronic endoscope system that can acquire a high-quality endoscope observation image by performing sufficient noise reduction processing even if an image capture environment changes. A noise reduction processing unit sets a pixel of interest and a neighboring pixel out of a plurality of pixels that constitute an endoscope observation image, and performs noise reduction processing on the pixel of interest according to a magnitude relationship between: a difference in pixel value between the pixel of interest and the neighboring pixel; and a reference threshold value. A reference threshold value changing processing unit changes the reference threshold value for noise reduction processing based on a ratio between at least two color components that are included in the pixel of interest.

10 Claims, 5 Drawing Sheets

(51) Int. Cl.
*A61B 1/00* (2006.01)
*G02B 23/24* (2006.01)
*H04N 7/18* (2006.01)
*G06T 7/136* (2017.01)
*A61B 1/05* (2006.01)
*A61B 1/06* (2006.01)
*G06T 5/50* (2006.01)
*H04N 5/213* (2006.01)
*H04N 5/357* (2011.01)

(52) U.S. Cl.
CPC .......... *A61B 1/00186* (2013.01); *A61B 1/045* (2013.01); *A61B 1/05* (2013.01); *A61B 1/0646* (2013.01); *A61B 1/0669* (2013.01); *G02B 23/2469* (2013.01); *G06T 7/136* (2017.01); *H04N 7/183* (2013.01); *G06T 5/50* (2013.01); *G06T 2207/10024* (2013.01); *G06T 2207/10068* (2013.01); *G06T 2207/20024* (2013.01); *G06T 2207/20224* (2013.01); *H04N 5/213* (2013.01); *H04N 5/357* (2013.01)

(58) Field of Classification Search
USPC ................................................ 382/162–172
See application file for complete search history.

(56) References Cited

U.S. PATENT DOCUMENTS

| | | | |
|---|---|---|---|
| 2006/0104538 A1* | 5/2006 | Izumi | G06T 5/002 382/275 |
| 2008/0144960 A1 | 6/2008 | Watarai | |
| 2011/0181752 A1* | 7/2011 | Nakashima | H04N 9/045 348/223.1 |
| 2013/0100263 A1 | 4/2013 | Tsuda | |
| 2015/0071564 A1 | 3/2015 | Sasaki | |

FOREIGN PATENT DOCUMENTS

| | | |
|---|---|---|
| JP | 2014-003462 | 1/2014 |
| JP | 2015-223249 | 12/2015 |

OTHER PUBLICATIONS

International Search Report (ISR) and Written Opinion from International Searching Authority (Japan Patent Office) in International Pat. Appl. No. PCT/IB2017/054320, dated Oct. 17, 2017, together with an English language ISR.

* cited by examiner

IMAGE PROCESSING APPARATUS AND ELECTRONIC ENDOSCOPE SYSTEM

TECHNICAL FIELD

The present invention relates to an image processing apparatus and an electronic endoscope system.

BACKGROUND ART

Patent Document 1 discloses an electronic endoscope system that acquires, as endoscope observation images, normal observation images captured using normal light, and narrow-band observation images captured using narrow-band light having a bandwidth narrower than that of normal light, and displays the endoscope observation images.

Patent Document 2 discloses an image processing apparatus and an image processing method for executing image noise reduction processing using a technology called ε filter. The ε filter technology is used to perform noise reduction processing on a pixel of interest, by setting a pixel of interest and neighboring pixels out of a plurality of pixels that constitute an image, and perform averaging using only a portion in which the difference in pixel value between the pixel of interest and each neighboring pixel is smaller than or equal to a reference threshold value, while leaving a high-frequency component in which the difference in pixel value between the pixel of interest and each neighboring pixel is greater than a reference threshold value.

PRIOR ART DOCUMENTS

Patent Documents

Patent Document 1: JP 2015-223249A
Patent Document 2: JP 2008-124976A

SUMMARY OF INVENTION

Problem to be Solved by Invention

However, in observation using an endoscope, cases in which an image capture environment significantly changes often occur, e.g. a case in which switching from normal light observation using normal light to narrow-band light observation using narrow-band light occurs, and a case in which chemicals such as indigo carmine and iodine are sprayed. If a conventional ε filter having a threshold that can be determined in advance is applied as it is to endoscope image processing, there is the risk of noise reduction processing not being sufficiently performed due to changes in an image capture environment, which leads to the risk of the quality of endoscope observation images degrading.

The present invention is made based on awareness of the problems above, and one object thereof is to provide an image processing apparatus and an electronic endoscope system that can acquire high-quality endoscope observation images by performing sufficient noise reduction processing even if an image capture environment changes.

Means for Solving Problem

An image processing apparatus according to one aspect of the present invention includes: a noise reduction processing unit that sets a pixel of interest and a neighbouring pixel out of a plurality of pixels that constitute an endoscope observation image, and performs noise reduction processing on the pixel of interest according to a magnitude relationship between: a difference in pixel value between the pixel of interest and the neighbouring pixel; and a reference threshold value; and a reference threshold value changing processing unit that changes the reference threshold value for the noise reduction processing based on a ratio between at least two color components that are included in the pixel of interest.

An electronic endoscope system according to one aspect of the present invention includes: an electronic endoscope that acquires an endoscope observation image; and an image processing apparatus that performs image processing on the endoscope observation image. The image processing apparatus includes: a noise reduction processing unit that sets a pixel of interest and a neighbouring pixel out of a plurality of pixels that constitute the endoscope observation image, and performs noise reduction processing on the pixel of interest according to a magnitude relationship between: a difference in pixel value between the pixel of interest and the neighbouring pixel; and a reference threshold value; and a reference threshold value changing processing unit that changes the reference threshold value for the noise reduction processing based on a ratio between at least two color components that are included in the pixel of interest.

The reference threshold value changing processing unit can change the reference threshold value for the noise reduction processing based on a ratio between a G (Green) component and a B (Blue) component that are included in the pixel of interest.

The reference threshold value changing processing unit can divide a GB plane that has two orthogonal axes indicating the G component and the B component into a plurality of areas, using an inclined straight line that passes through an origin, and change the reference threshold value for the noise reduction processing according to which area the ratio between the G component and the B component included in the pixel of interest belongs to, out of the plurality of areas of the GB plane.

The noise reduction processing unit and the reference threshold value changing processing unit can perform the noise reduction processing on each of the plurality of pixels while changing the reference threshold value.

The noise reduction processing unit and the reference threshold value changing processing unit can perform the noise reduction processing on an entirety of the plurality of pixels or on each of a plurality of pixel groups that are divided from the plurality of pixels, while changing the reference threshold value.

Advantageous Effects of Invention

With the present invention, it is possible to provide an image processing device and an electronic endoscope system that can acquire high-quality endoscope observation images by performing sufficient noise reduction processing even if an image capture environment changes.

DESCRIPTION OF EMBODIMENTS

Figure 1:
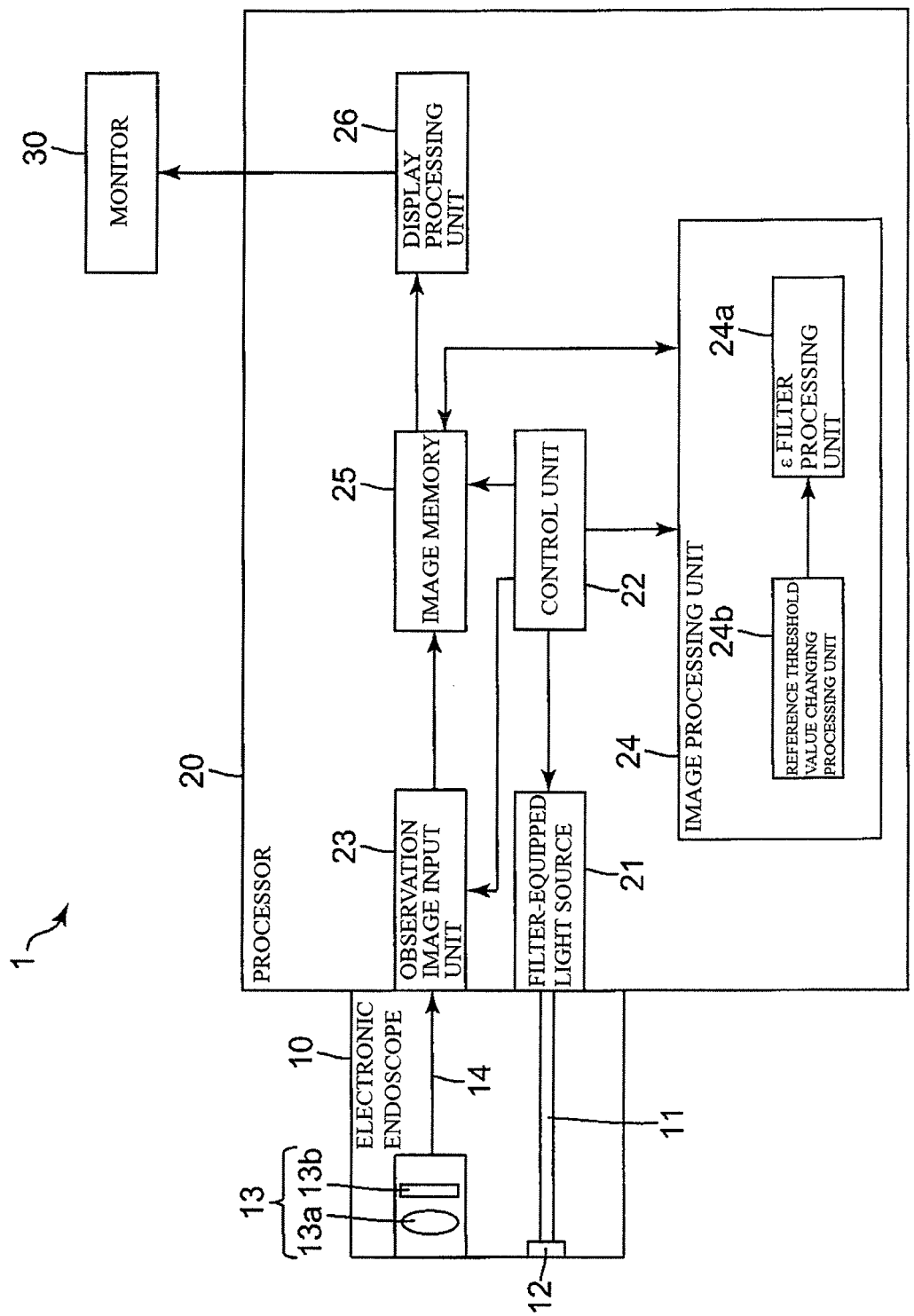
FIG. 1 is a block diagram showing a configuration of an electronic endoscope system according to an embodiment of the present invention.

The following describes an electronic endoscope system 1 according to an embodiment of the present invention with reference to FIGS. 1 to 6. As shown in FIG. 1, the electronic endoscope system 1 includes an electronic endoscope 10, a processor (an image processing apparatus and a light source apparatus) 20, and a monitor 30.

Although details of the shape of the electronic endoscope 10 are omitted from FIG. 1, the electronic endoscope 10 includes a grip and control portion that is to be gripped by an operator, an insertion portion that is flexible and extends from the grip and control portion, a universal tube that extends from the grip and control portion in a direction away from the insertion portion, and a connector that is provided at the leading end of the universal tube.

Light-guide fibers 11 are built into the electronic endoscope 10. The light-guide fibers 11 extend to the inside of the connector via the insertion portion, the grip and operation portion, and the universal tube of the electronic endoscope 10. The connector of the electronic endoscope 10 is connected to a connector of the processor 20, and thus the electronic endoscope 10 and the processor 20 are optically connected to each other. Illumination light (normal light or narrow-band light described below) from a filter-equipped light source 21, which is built into the processor 20, is guided inside the light-guide fibers 11, and is emitted outward from an illumination lens 12, which is provided at the leading end of the insertion portion of the electronic endoscope 10, according to a predetermined light distribution pattern.

The filter-equipped light source 21 includes a high-intensity lamp (e.g. a xenon lamp, a halogen lamp, a mercury lamp, or a metal halide lamp) that emits white light that includes wavelength bands respectively corresponding to R (Red), G (Green), and B (blue). The filter-equipped light source 21 also includes a filter unit that is located on the light path of the white light emitted from the high-intensity lamp. The filter unit includes a rotary filter turret that is provided with a filter for the color white, which allows white light from the high-intensity lamp to pass, thereby generating normal light, and a narrow-band filter, which narrows the wavelength band of the white light emitted from the high-intensity lamp, thereby generating narrow-band light. The narrow-band filter has a spectral transmittance with a narrow width at half maximum, for each of the R, G and B wavelength bands. The rotary filter turret of the filter unit is driven to rotate, and thus white light from the high-intensity lamp alternatingly passes through the filter for the color white and the narrow-band filter, and normal light and narrow-band light that has a bandwidth narrower than that of normal light are alternatingly emitted from the filter-equipped light source 21. The wavelength band of narrow-band light can be set as desired as long as it is narrower than the wavelength band of normal light. For example, narrow-band light may have a wavelength band that matches the spectral properties of hemoglobin. The filter-equipped light source 21 is well known as disclosed in Patent Document 2 above, for example, and therefore a further detailed description thereof is omitted.

An imaging unit 13 is provided at the leading end of the insertion portion of the electronic endoscope 10. The imaging unit 13 is composed of a plurality of constituent elements that include an objective lens 13a and a CCD 13b that captures a subject image that has passed through the objective lens 13a, and are integrated into one piece using a resin material such as an epoxy resin. The CCD 13b alternatingly acquires a normal observation image signal and a narrow-band observation image signal that are respectively based on normal light and narrow-band light that are alternatingly emitted from the filter-equipped light source 21 via the light-guide fibers 11 and the illumination lens 12. The normal observation image signal and the narrow-band observation image signal are transmitted to the processor 20 via a signal transmission cable 14.

The processor 20 includes a control unit 22, an observation image input unit (an image input processing unit) 23, an image processing unit (a computation unit) 24, an image memory 25, and a display processing unit 26. The control unit 22 totally controls all of the constituent elements of the processor 20.

The observation image input unit 23 performs input processing on the normal observation image signal and the narrow-band observation image signal transmitted from the signal transmission cable 14 of the electronic endoscope 10 so that the signals are input thereto as a normal observation image and a narrow-band observation image. The normal observation image and the narrow-band observation image input to the observation image input unit 23 are "endoscope observation images".

The image processing unit 24 performs image processing on the endoscope observation images input to the observation image input unit 23. The image processing unit 24 includes a ε filter processing unit (a noise reduction processing unit) 24a and a reference threshold value changing processing unit (a threshold value calculation unit) 24b.

The ε filter processing unit 24a sets a pixel of interest and neighboring pixels out of a plurality of pixels that constitute an endoscope observation image, and performs noise reduction processing on the pixel of interest according to the magnitude relationship between: the difference in pixel value between the pixel of interest and each neighboring pixel; and a reference threshold value.

Figure 2:
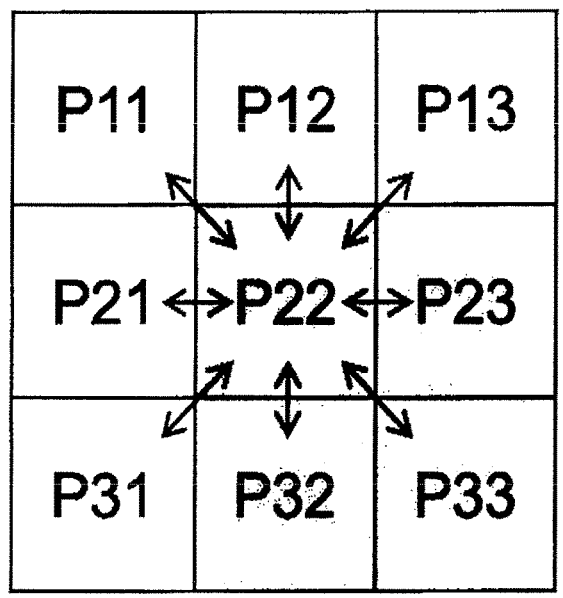
FIG. 2 is a conceptual diagram showing noise reduction processing performed by a ε filter processing unit.

FIG. 2 is a conceptual diagram showing noise reduction processing performed by the e filter processing unit 24a. In the example shown in the diagram, the plurality of pixels that constitute an endoscope observation image are 3×3=9 pixels (P11, P12, P13, P21, P22, P23, P31, P32, and P33), in which a pixel P22 that is at the center of the plurality of pixels is defined as the pixel of interest, and eight pixels P11, P12, P13, P21, P23, P31, P32, and P33 that are adjacent to the pixel of interest P22 are defined as the neighboring pixels. Note that the relationship between the pixel of interest and the neighboring pixels is not limited to the example above, and may be set as desired. For example, only one or more pixels out of the pixels that are adjacent to the pixel of interest may be defined as the neighboring pixels, or pixels that are not adjacent to, but surround the pixel of interest (e.g. skip one pixel) may be defined as the neighboring pixels.

The ε filter processing unit 24a calculates the difference between the pixel of interest P22 and each of the neighboring pixels P11, P12, P13, P21, P23, P31, P32, and P33, and determines whether or not the difference is greater than or equal to a reference threshold value. In the example shown in FIG. 2, the pixel of interest P22 and the neighboring pixels P23, P32, and P33 for which the above-described difference is greater than or equal to the reference threshold value are depicted on a gray background, and the neighboring pixels P11, P12, P13, P21, and P31 for which the above-described difference is smaller than the reference threshold value are depicted on a white background. The ε filter processing unit 24a calculates the average for the pixel of interest P22 and the neighboring pixels P11, P12, P13, P21, and P31 for which the above-described difference is smaller than the reference threshold value, to obtain a new pixel of interest (a pixel of interest after correction) P22' with reduced noise. The neighboring pixels P23, P32, and P33 for which the above-described difference is greater than or equal to the reference threshold value can possibly be, for example, edge portions or the like, and using these neighboring pixels to perform averaging can possibly cause the endoscope observation image to appear blurred. Hence, it is possible to perform high-accuracy noise reduction processing by discarding the neighboring pixels P23, P32, and P33 for which the above-described difference is greater than or equal to the reference threshold value. A specific formula for obtaining P22' is as follows:

$$P22'=(P11+P12+P13+P21+P31+P22)/6$$

The reference threshold value changing processing unit 24b changes a reference threshold value that is used by the ε filter processing unit 24a to perform noise reduction processing, based on the ratio between a G component and a B component, out of the R (Red) component, the G (Green) component and the B (Blue) component included in the pixel of interest (P22 in the above-described example).

Figure 3:
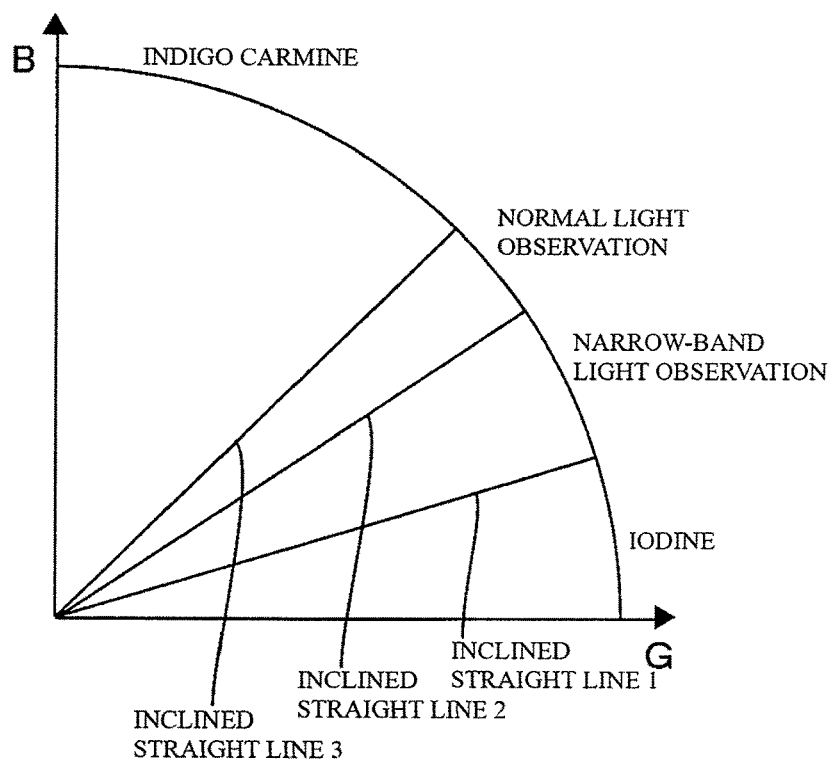
FIG. 3 is a conceptual diagram showing reference threshold value changing processing performed by a reference threshold value changing processing unit.

FIG. 3 is a conceptual diagram showing reference threshold value changing processing performed by the reference threshold value changing processing unit 24b. As shown in the drawing, the reference threshold value changing processing unit 24b divides a GB plane, which has two orthogonal axes indicating the G component and the B component, into four areas using three inclined straight lines that pass through the origin, and changes the reference threshold value that is used by the e filter processing unit 24a to perform noise reduction processing, according to which area the ratio between the G component and the B component included in the pixel of interest belongs to, out of the four areas of the GB plane.

In this example, in the case where the B component takes a constant value, the straight line with the smallest inclination (the ratio of the G component is the largest) is defined as an inclined straight line 1, the straight line with the second smallest inclination (the ratio of the G component is the second largest) is defined as an inclined straight line 2, and the straight line with the largest inclination (the ratio of the G component is the smallest) is defined as an inclined straight line 3.

From experience in various kinds of sampling or the like, the inventors of the present invention found that the observation environment (the image capture environment) corresponding to the area below the inclined straight line 1 is in "an iodine-sprayed observation state", the observation environment corresponding to the area between the inclined straight line 1 and the inclined straight line 2 is in "an narrow-band light observation state", the observation environment corresponding to the area between the inclined straight line 2 and the inclined straight line 3 is in "a normal light observation state", and the observation environment corresponding to the area above the inclined straight line 3 is in "an indigo carmine-sprayed observation state".

For example, the reference threshold value changing processing unit 24b can set the reference threshold value to be the largest when the observation environment is in "the iodine-sprayed observation state", set the reference threshold value to be the smallest when the observation environment is in "the narrow-band light observation state", set the reference threshold value to be the second largest when the observation environment is in "the normal light observation state", and set the reference threshold value to be the third largest when the observation environment is in "the indigo carmine-sprayed observation state". This is because, in the narrow-band light observation state and the indigo carmine-sprayed observation state, minute features are emphasized, and it is preferable that the reference threshold value is not too large (i.e. minute features are also caused to appear blurred if the reference threshold value is too large), whereas, in the iodine-sprayed observation state, minute features are not captured and the image appears darker (contains a larger amount of noise) than in the normal light observation state, and it is preferable that the reference threshold value is set to be relatively large.

Note that, in FIG. 3, the number of inclined straight lines that pass through the origin and the number of areas divided by the inclined straight lines can be determined as desired, and various design changes are applicable. For example, the GB plane may be divided into two areas using one inclined straight line, and the GB plane may be divided into three areas using two inclined straight lines. That is, the GB plane can be divided into n+1 areas using n inclined straight lines (n is a positive integer). Also, the observation environment (the image capture environment) that is to be identified is not limited to those shown in FIG. 3 (the iodine-sprayed state, the narrow-band light state, the normal observation state, and the indigo carmine-sprayed state), and various design changes are applicable.

In this way, the ε filter processing unit 24a and the reference threshold value changing processing unit 24b of the image processing unit 24 perform noise reduction processing on each of the plurality of pixels constituting the endoscope observation image while changing the reference threshold value.

Figure 4:
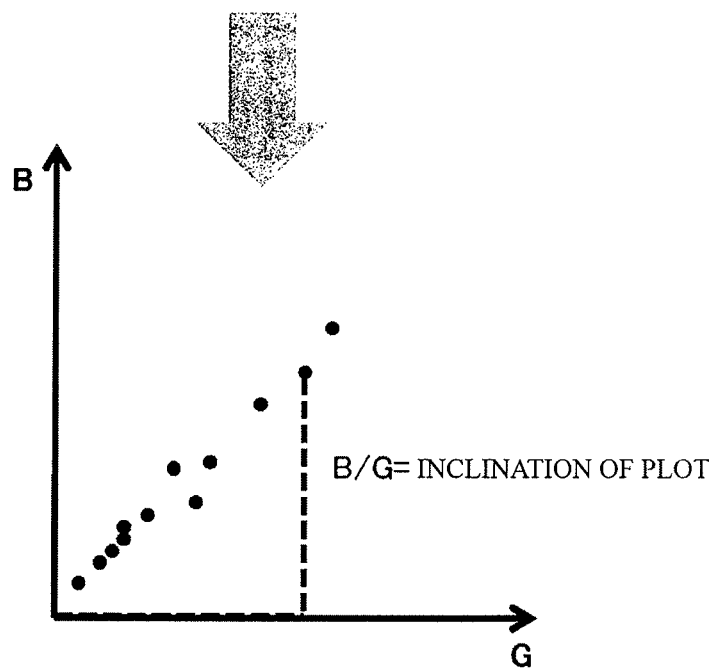
FIG. 4 is a diagram showing pixels that constitute a normal observation image, plotted on a GB plane.
Figure 5:
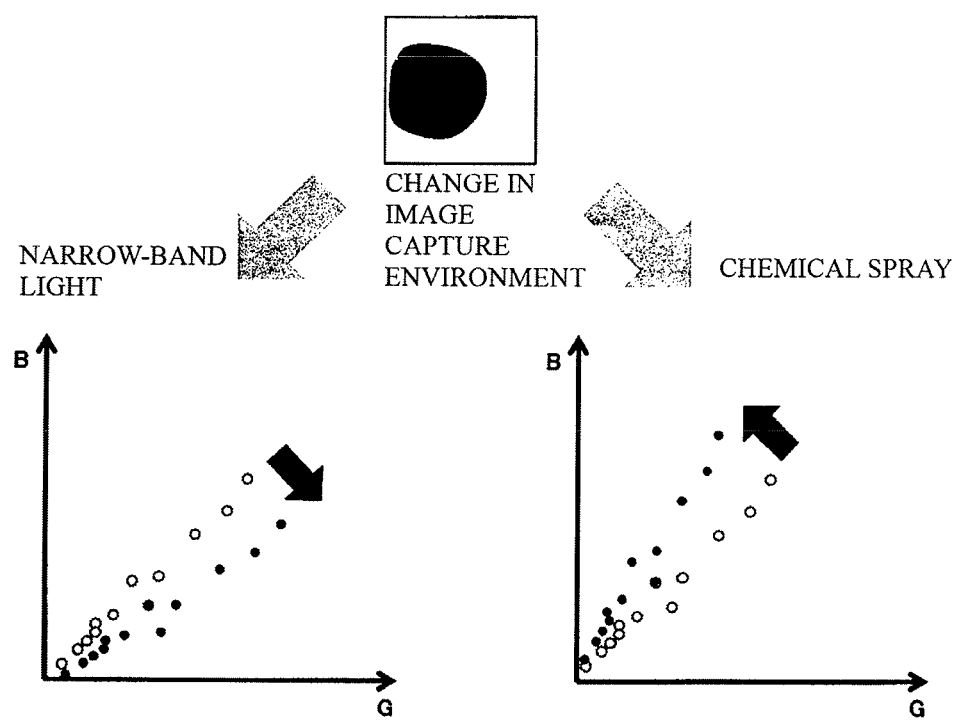
FIG. 5 is a diagram showing changes in the plotted pixels when transition from a normal observation state to a narrow-band observation state or a chemical-sprayed state (indigo carmine-sprayed state) occurs.

FIG. 4 is a diagram showing the pixels that constitute a normal observation image, plotted on the GB plane. FIG. 5 is a diagram showing changes in the plotted pixels when transition from the normal observation state to the narrow-band observation state or the chemical-sprayed state (the indigo carmine-sprayed state) occurs.

Since the R component is dominant in the endoscope observation image, the value of the G component and the value of the B component change at substantially the same rate, and the plot on the GB plane substantially has the shape of a straight line. The inclination of this straight line (B/G) can be interpreted as a feature value and is used to identify the observation environment (the image capture environment).

As shown in FIG. 4, in the case of a normal observation image, the ratio between the G component and the B component is approximately 1:1, and the inclination of the straight line is close to 1. In contrast, as shown in FIG. 5, if transition from the normal observation state to the narrow-band observation state or the chemical-sprayed state (the indigo carmine-sprayed state) occurs, the G component and the B component become unbalanced and the inclination of the straight line changes to be smaller or greater than 1. In such a context, it is possible to achieve the optimum noise reduction effect by deducing the current observation environment (image capture environment) from the value of the inclination of the straight line, and setting one of reference threshold values that have been respectively prepared for the observation environments (see FIG. 3).

It is possible to separately calculate the above-described inclination (B/G) of the straight line for each pixel. Alternatively, it is also possible to calculate the average of inclinations in the entire image, obtain the reference threshold value corresponding to this average, regarding the average as the inclination that is to be applied to the entire image (the representative inclination of the image), and uniformly apply the reference threshold value to the entire image. That is, the method for setting the inclined straight lines in FIG. 3 can be determined as desired, and various design changes are applicable.

The image memory 25 stores an endoscope observation image that has undergone image processing performed by the image processing unit 24. The display processing unit 26 displays the endoscope observation image stored in the image memory 25 on the monitor 30.

Figure 6:
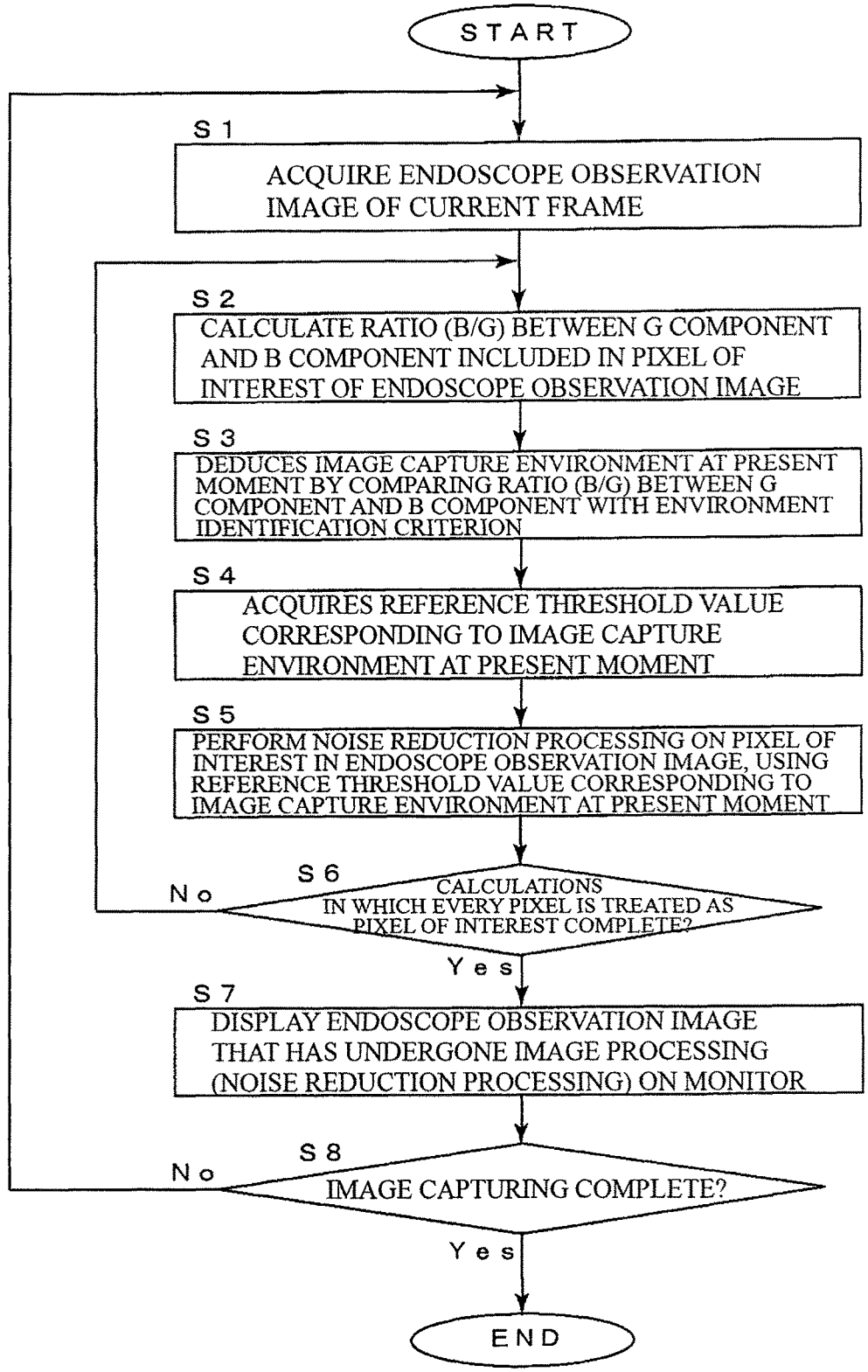
FIG. 6 is a flowchart showing image processing according to the embodiment of the present invention.

The following describes image processing performed by the electronic endoscope system 1 and the processor 20 according to the present embodiment with reference to the flowchart shown in FIG. 6.

In step S1, the image processing unit 24 acquires an endoscope observation image of the current frame.

In step S2, the reference threshold value changing processing unit 24b of the image processing unit 24 calculates the ratio (B/G) between the G component and the B component included in the pixel of interest of the endoscope observation image acquired in step S1.

In step S3, the reference threshold value changing processing unit 24b of the image processing unit 24 deduces the image capture environment at the present moment by comparing the ratio (B/G) between the G component and the B component calculated in step S2 with an environment identification criterion. For example, the reference threshold value changing processing unit 24b of the image processing unit 24 deduces in which state the image capture environment at the present moment is, out of the above-described iodine-sprayed state, narrow-band light state, normal observation state, and indigo carmine-sprayed state, based on which area the plot defined by the ratio (B/G) between the G component and the B component calculated in step S2 belongs to, out of the areas of the GB plane.

In step S4, the reference threshold value changing processing unit 24b of the image processing unit 24 acquires (sets) the reference threshold value corresponding to the image capture environment at the present moment deduced in step S3.

In step S5, the ε filter processing unit 24a of the image processing unit 24 performs noise reduction processing on the pixel of interest in the endoscope observation image, using the reference threshold value acquired in step S4.

In step S6, the image processing unit 24 determines whether or not calculations in which every pixel of the endoscope observation image is treated as the pixel of interest have been completed. If it is determined that the calculations in which every pixel of the endoscope observation image is treated as the pixel of interest have been completed (step S6: Yes), step S7 is performed next. If it is determined that the calculations in which every pixel of the endoscope observation image is treated as the pixel of interest have not been completed (step S6: No), the pixel of interest in the endoscope observation image is shifted, and the processing loop from step S2 to step S5 is repeated.

In step S7, the display processing unit 26 displays, on the monitor 30, the endoscope observation image that has undergone image processing performed by the image processing unit 24 (that has undergone noise reduction processing performed by the ε filter processing unit 24a and the reference threshold value changing processing unit 24b).

In step S8, it is determined whether or not image capturing performed by the electronic endoscope system 1 is complete. If it is determined that image capturing performed by the electronic endoscope system 1 is complete (step S8: Yes), processing is terminated. If it is determined that image capturing performed by the electronic endoscope system 1 is not complete (is ongoing) (step S8: No), the processing loop from step S1 to step S7 is repeated.

As described above, with the electronic endoscope system 1 and the processor 20 according to the present embodiment, the ε filter processing unit (the noise reduction processing unit) 24a sets a pixel of interest and neighboring pixels out of a plurality of pixels that constitute an endoscope observation image, and performs noise reduction processing on the pixel of interest according to the magnitude relationship between: the difference in pixel value between the pixel of interest and each neighboring pixel; and a reference threshold value, and the reference threshold value changing processing unit 24b changes the reference threshold value for noise reduction processing, based on a ratio between at least two color components that are included in the pixel of interest. Consequently, it is possible to acquire a high-quality endoscope observation image by performing sufficient noise reduction processing even if the observation environment (the image capture environment) changes.

More specifically, the electronic endoscope system 1 and the processor 20 according to the present embodiment automatically detect narrow-band light observation and chemical spray when they are performed, and automatically correct the reference threshold value, thereby achieving the optimum noise reduction effect without the need for a user operation. That is, with the present embodiment, the optimum reference threshold value is dynamically set (in real time) according to changes in the observation environment (the image capture environment).

The embodiment above describes an example in which the reference threshold value changing processing unit 24b changes the reference threshold value for noise reduction processing based on the ratio between the G component and the B component included in the pixel of interest. However, the index that can be used to change the reference threshold value is not limited in such a manner, and various design changes are applicable. For example, the reference threshold value changing processing unit 24b may change the reference threshold value for noise reduction processing based on the ratio (G/R) between the G component and the R component included in the pixel of interest, or the ratio (B/R) between the B component and the R component included in the pixel of interest. Furthermore, the reference threshold value changing processing unit 24b may convert RGB to YCbCr or the like in another color space, and then use the ratio between them. That is, the reference threshold value changing processing unit 24b only needs to change the reference threshold value for noise reduction processing based on the ratio between at least two color components that are included in the pixel of interest.

The embodiment above describes an example in which the ε filter processing unit 24a and the reference threshold value changing processing unit 24b of the image processing unit 24 perform noise reduction processing on each of the plurality of pixels that constitute the endoscope observation image, while changing the reference threshold value. However, the ε filter processing unit 24a and the reference threshold value changing processing unit 24b of the image processing unit 24 may perform noise reduction processing on the entirety of the plurality of pixels that constitute the endoscope observation image, or on each of a plurality of pixel groups that are divided from the plurality of pixels, while changing the reference threshold value.

The embodiment above describes an example of noise reduction processing performed by the ε filter processing unit 24a of the image processing unit 24 using the ε filter technology. However, the algorithm that can be used to perform noise reduction processing is not limited to the ε filter. That is, any algorithm may be employed as along as noise reduction processing is performed on the pixel of interest according to the magnitude relationship between: the difference in pixel value between the pixel of interest and each neighboring pixel; and a reference threshold value. For example, in addition to the ε filter, the present invention may be applied to a digital filter that uses the difference in pixel value between the pixel of interest and each neighbouring pixel, such as a bilateral filter.

The embodiment above describes an example in which noise reduction processing is performed on an RGB image that has undergone so-called demosaicing. However, noise reduction processing may be performed on a RAW image that has not been undergone demosaicing. If noise reduction processing is performed on a RAW image that has not undergone demosaicing, necessary information is acquired from a pixel in the vicinity or an RGB image of the previous frame so that the ratio (B/G) between the B component and the G component can be calculated.

INDUSTRIAL APPLICABILITY

The image processing apparatus and the electronic endoscope system according to the present invention can be preferably employed as an image processing apparatus and an electronic endoscope system in the field of medical endoscopes, for example.

DESCRIPTION OF REFERENCE SIGNS

1 Electronic Endoscope System
10 Electronic Endoscope
11 Light-guide Fibers
12 Illumination Lens
13 Imaging Unit
13a Objective Lens
13b CCD
14 Signal Transmission Cable
20 Processor (Image Processing Apparatus, Light Source Apparatus)
21 Filter-Equipped Light Source
22 Control Unit
23 Observation Image Input Unit (Image Input Processing Unit)
24 Image Processing Unit (Computation Unit)
24a ε Filter Processing Unit (Noise Reduction Processing Unit)
24b Reference Threshold Value Changing Processing Unit (Threshold Value Calculation Unit)
25 Image Memory
26 Display Processing Unit
30 Monitor

The invention claimed is:

1. An image processing apparatus comprising:
a noise reduction processor that sets a pixel of interest and a neighbouring pixel out of a plurality of pixels that constitute an endoscope observation image, and performs noise reduction processing on the pixel of interest according to a magnitude relationship between: a difference in pixel value; and a reference threshold value; and
a reference threshold value changing processor that changes the reference threshold value for the noise reduction processing based on a ratio between at least two color components that are included in the pixel of interest,
wherein the difference in pixel value is between the pixel of interest and the neighbouring pixel.

2. The image processing apparatus according to claim 1, wherein the reference threshold value changing processor changes the reference threshold value for the noise reduction processing based on a ratio between a green component and a blue component that are included in the pixel of interest.

3. The image processing apparatus according to claim 2, wherein the reference threshold value changing processor divides a GB plane that has two orthogonal axes indicating the green component and the blue component into a plurality of areas, using an inclined straight line that passes through an origin, and changes the reference threshold value for the noise reduction processing according to which area the ratio between the green component and the blue component included in the pixel of interest belongs to, out of the plurality of areas of the GB plane.

4. The image processing apparatus according to claim 1, wherein the noise reduction processor and the reference threshold value changing processor perform the noise reduction processing on each of the plurality of pixels while changing the reference threshold value.

5. The image processing apparatus according to claim 1, wherein the noise reduction processor and the reference threshold value changing processor perform the noise reduction processing on an entirety of the plurality of pixels or on each of a plurality of pixel groups that are divided from the plurality of pixels, while changing the reference threshold value.

6. An electronic endoscope system comprising:
an electronic endoscope that acquires an endoscope observation image; and
an image processing apparatus that performs image processing on the endoscope observation image,
wherein the image processing apparatus comprises:
a noise reduction processor that sets a pixel of interest and a neighbouring pixel out of a plurality of pixels that constitute the endoscope observation image, and performs noise reduction processing on the pixel of interest according to a magnitude relationship between: a difference in pixel value; and a reference threshold value; and
a reference threshold value changing processor that changes the reference threshold value for the noise reduction processing based on a ratio between at least two color components that are included in the pixel of interest,
wherein the difference in pixel value is between the pixel of interest and the neighbouring pixel.

7. The electronic endoscope system according to claim 6, wherein the reference threshold value changing processor changes the reference threshold value for the noise reduction processing based on a ratio between a green component and a blue component that are included in the pixel of interest.

8. The electronic endoscope system according to claim 7, wherein the reference threshold value changing processor divides a GB plane that has two orthogonal axes indicating the green component and the blue component into a plurality of areas, using an inclined straight line that passes through an origin, and changes the reference threshold value for the noise reduction processing according to which area the ratio between the green component and the blue component included in the pixel of interest belongs to, out of the plurality of areas of the GB plane.

9. The electronic endoscope system according to claim 6, wherein the noise reduction processor and the reference threshold value changing processor perform the noise reduction processing on each of the plurality of pixels while changing the reference threshold value.

10. The electronic endoscope system according to claim 6, wherein the noise reduction processor and the reference threshold value changing processor perform the noise reduction processing on an entirety of the plurality of pixels or on each of a plurality of pixel groups that are divided from the plurality of pixels, while changing the reference threshold value.

\* \* \* \* \*